United States Patent [19]

Carter

[11] Patent Number: 4,789,757
[45] Date of Patent: Dec. 6, 1988

[54] N-FORMYLATION OF AMINO CARBOXYLIC COMPOUNDS WITH FORMAMIDE

[75] Inventor: Charles G. Carter, Columbia, Md.

[73] Assignee: W. R. Grace & Co.-Conn., New York, N.Y.

[21] Appl. No.: 74,751

[22] Filed: Jul. 17, 1987

[51] Int. Cl.$^4$ .............................................. C07C 99/00
[52] U.S. Cl. .................................. 562/445; 562/450; 562/571; 562/575
[58] Field of Search ............... 562/450, 574, 445, 571, 562/575

[56] References Cited

FOREIGN PATENT DOCUMENTS 3145736  5/1983  Fed. Rep. of Germany ...... 562/450

OTHER PUBLICATIONS

Takatori, Chem. Abst., vol. 104, #58775 (1986).
Meisser et al, Chem. Abst., vol. 105, #190686k (1986).
Vilvala, Chem. Abst., vol. 89, #163,231c (1978).
Gensler et al.; J. Org. Chem.; "Cinnamic Acids from Tetrahydroisoquinoline Carboxylic Acids"; vol. 21, pp. 336, 1956.
King et al.; J. Chem. Soc.; "Synthesis from Phthalimido-Acids"; p. 880, 1957.
Sheehan et al.; J. Am. Chem. Soc.; "The Use of N-Formylamino Acids in Peptide Synthesis"; vol. 80, p. 1154, 1958.

Primary Examiner—James H. Reamer
Attorney, Agent, or Firm—Jill H. Krafte

[57] ABSTRACT

The amine nitrogen of an amino carboxylic acid is formylated by reacting the amino carboxylic acid with formamide.

11 Claims, No Drawings

N-FORMYLATION OF AMINO CARBOXYLIC COMPOUNDS WITH FORMAMIDE

BACKGROUND OF THE INVENTION

The invention relates to N-formylation of certain amino carboxylic acids. An amino carboxylic acid, e.g., aspartic acid, is reacted with formamide to convert the amine group to a formyl group, -NH-CHO. With the amine group protected (by the N-formylation), the compound can then be used in conventional dipeptide synthesis or in other chemical or enzymatic reactions. The protecting formyl group may be removed by mild hydrolysis.

N-formylation of amino carboxylic acids is not new and a number of reagents have been employed to protect the amine group in this manner. However, the prior art processes are complex, expensive and/or do not provide adequate yields. For example: L-phenylalanine has been N-formylated by treating its sodium salt with chloral, Chem. Abs. 102(11):96080z. D-phenylalanine, glycine, valine and glutamic acid have been N-formylated with $HCO_2.SO_3.Na$, Chem. Abs. 85(1):6043t. Acetic anhydride has been added to amino acid in formic acid, Sheehan et al., J. Am. Chem. Soc., Vol. 80, p. 1154 (1958); Gensler et al., J. Org. Chem., Vol. 21, p. 336 (1956). Benzyl esters of amino acid derivatives can be N-formylated with formic acid in the presence of N,N'-dicyclohexylcarbodiimide, Thomas, Tetrah. Let. 335 (1967). N-formylation of t-butylamine with ethyl formate has been reported in yields of 29.4 to 84%, Moffatt et al., J. Org. Chem., Vol. 27, p. 4058 (1962). Pettit et al., J. Org. Chem., Vol. 24, p. 895 (1959), reports that sodium methoxide, aniline and dimethylformamide may be heated to yield formanilide. Galat et al., J. Am. Chem. Soc., Vol. 65, pp. 1566-67 (1944), disclose the reaction:

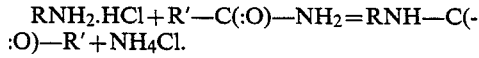

BRIEF DESCRIPTION OF THE INVENTION

N-formylation of amino carboxylic acids is achieved by reacting the amine carboxylic acid with formamide to convert the amine group to an N-formyl group.

It is a primary object of this invention to disclose a simple and direct method for the N-formylation of amino carboxylic acids. It is a related object to provide a method capable of high product yield.

DETAILED DESCRIPTION OF THE INVENTION

A novel process for N-formylating amino carboxylic acids is disclosed. The process comprises reacting an amino carboxylic acid with formamide, thereby forming the corresponding N-formyl amino carboxylic acid.

In this description, the term "amino carboxylic acid" refers to compounds that carry one or more amine groups and one or more carboxylic groups. The amino nitrogen may be a ring member. Suitable amino carboxylic compounds include those with one amine and one carboxylic group, e.g., glycine, alanine, aminobutyric acid, valine, and the like. Such compounds fall with with the genus $H_2N$-R-COOH, where R is a linear or branched alkylene with 1 to 10 carbons. Suitable compounds with one amine and one carboxylic group also include serine, threonine, phenylalanine, tyrosine, and the like. These materials carry hydroxyl and/or aromatic substituents. Compounds with one amine and two carboxylic groups are especially suitable, e.g., aminomalonic acid, aspartic acid, glutamic acid, and the like.

The naturally occurring amino carboxylic acids are well known: alanine, arginine, asparagine, aspartic acid, cysteine, cystine, 3,5-dibromotyrosine, 3,5-diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophan, tyrosine and valine.

As used herein, "N-formylation" means that the amino nitrogen is converted to an N-formyl group by acquisition of $-C(:O)H$ from formamide:

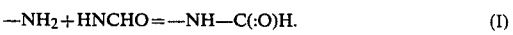

In the case where the amine is a secondary amine, e.g., where the nitrogen is a ring nitrogen, the N-formyl group is

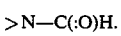

The reaction of this invention can be illustrated by the formylation of aspartic acid:

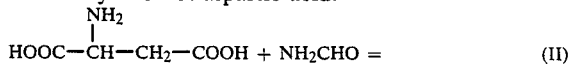

The N-formylation of this invention is suitably carried out with a stoichiometric excess of formamide, preferably a considerable excess. The reaction mixture is heated to temperatures of about 50° to about 120° C., preferably about 60° to 100° C. The reaction preferably is conducted under an inert atmosphere, such as nitrogen, for example. Reaction progress can be followed by NMR or other convenient analytical means. Reaction times may range from about fifteen minutes to about 24 hours. The reaction is often completed within an hour or so. Simply heating a slurry or solution of the amino carboxylic acid in formamide will make some N-formyl product. Stirring is preferred.

The mole ratio of amino carboxylic acid:formamide is suitably about 1:4 to about 1:20. If there are two or more amine groups on the amino carboxylic acid (e.g., arginine, asparagine, cystine, etc.) the amount of formamide should be increased proportionately.

The N-formylated product can be recovered by conventional isolation procedures such as recrystallization from an appropriate solvent. Following use of the N-formylated product (e.g., in dipeptide synthesis), the N-formyl group can be returned to the amine form by mild hydrolysis as indicated elsewhere herein.

The N-formylated compounds made by this invention are valuable intermediates in dipeptide synthesis. These compounds may also have uses unrelated to dipeptide synthesis. For example, nicotinic acid can be synthesized from N-formyl-L-aspartate by extracts of *Clostridium butylicum*.

The following examples illustrate without limiting the invention.

EXAMPLE 1

N-Formyl-L-Aspartic Acid

Under a nitrogen atmosphere, a slurry of 2.7 gm (20 mmol) L-aspartic acid in 4.0 ml (100 mmol) formamide was heated at 95°–100° C. for 2 hours. Examination of the resulting homogeneous mixture by proton NMR showed that the L-aspartic acid had been completely converted to its N-formyl derivative.

EXAMPLE 2

N-Formyl-Glycine

Under a nitrogen atmosphere, a slurry of 0.75 gm (10 mmol) glycine in 4.0 ml (100 mmol) formamide was heated at 90° C. for 30 minutes. Examination of the resulting homogeneous mixture by proton NMR showed that the glycine had been completely converted to N-formyl glycine.

EXAMPLE 3

N-Formyl-Alanine

Under a nitrogen atmosphere, a slurry of 0.89 gm (10 mmol) alanine in 4.0 ml (100 mmol) formamide was heated at 90° C. for 65 minutes. Examination of the resulting homogeneous mixture by proton NMR showed an 80% conversion of the alanine to its N-formyl derivative.

EXAMPLE 4

N-Formyl-Phenylalanine

Under a nitrogen atmosphere, a slurry of 1.65 gm (10 mmol) phenylalanine in 4.0 ml (100 mmol) formamide was heated at 90° C. for 45 minutes. Examination of the resulting homogeneous solution by proton NMR showed an 85% conversion of the phenylalanine to its N-formyl derivative.

EXAMPLE 5

N-Formyl-Tyrosine

Under a nitrogen atmosphere, a slurry of 1.81 gm (10 mmol) tyrosine in 4.0 ml (100 mmol) formamide was heated at 90° C. for 19 hours and 10 minutes. Examination of the resulting homogeneous solution by proton NMR showed an 84% conversion of the tyrosine to its N-formyl derivative.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

I claim:

1. A process for N-formylating an amino carboxylic acid consisting of reacting a slurry of said amino carboxylic acid in formamide at temperatures from above about 50° C. to below 100° C.

2. The process of claim 1 in which the amino carboxylic acid is reacted with a stoichiometric excess of formamide.

3. The process of claim 2 in which a considerable stoichiometric excess of formamide is used.

4. The process of claim 1 which is conducted under an inert atmosphere.

5. The process of claim 1 in which the amino carboxylic acid is a naturally occurring amino carboxylic acid.

6. The process of claim 5 in which the amino carboxylic acid is aspartic acid, glycine, alanine, phenylalanine or tyrosine.

7. The process of claim 6 in which a slurry of L-aspartic acid in formamide is heated to form N-formyl-L-aspartic acid.

8. The process of claim 6 in which a slurry of glycine in formamide is heated to form N-formyl-glycine.

9. The process of claim 6 in which a slurry of L-phenylalanine in formamide is heated to form N-formyl-L-phenylalanine.

10. The process of claim 6 in which a slurry of L-alanine in formamide is heated to form N-formyl-L-alanine.

11. The process of claim 6 in which a slurry of L-tyrosine in formamide is heated to form N-formyl-L-tyrosine.

* * * * *